US009486504B2

(12) United States Patent
Raun et al.

(10) Patent No.: US 9,486,504 B2
(45) Date of Patent: Nov. 8, 2016

(54) REGULATION OF FOOD PREFERENCE USING GLP-1 AGONISTS

(75) Inventors: Kirsten Raun, Lyngby (DK); Pia Von Voss, Værløse (DK); Liselotte Bjerre Knudsen, Valby (DK); Kjell Malmlöf, Kalmar (SE)

(73) Assignee: Novo Nordisk A/S, Bagsvaerd (DK)

( * ) Notice: Subject to any disclaimer, the term of this patent is extended or adjusted under 35 U.S.C. 154(b) by 111 days.

(21) Appl. No.: 12/778,541

(22) Filed: May 12, 2010

(65) Prior Publication Data

US 2010/0222277 A1  Sep. 2, 2010

Related U.S. Application Data

(63) Continuation of application No. 11/448,545, filed on Jun. 7, 2006, now abandoned, which is a continuation of application No. PCT/DK2004/000853, filed on Dec. 9, 2004.

(60) Provisional application No. 60/529,480, filed on Dec. 15, 2003.

(30) Foreign Application Priority Data

Dec. 9, 2003  (DK) .................................. 2003 01816

(51) Int. Cl.
*A61K 38/26* (2006.01)
*A61K 38/22* (2006.01)

(52) U.S. Cl.
CPC ........... *A61K 38/26* (2013.01); *A61K 38/2278* (2013.01)

(58) Field of Classification Search
CPC ............................. C07K 14/605; A61K 38/26
See application file for complete search history.

(56) References Cited

U.S. PATENT DOCUMENTS

| | | | |
|---|---|---|---|
| 3,862,166 A | 1/1975 | Baklien et al. | |
| 5,118,666 A | 6/1992 | Habener | |
| 5,120,712 A | 6/1992 | Habener | |
| 5,380,872 A | 1/1995 | Sugg et al. | |
| 5,418,218 A | 5/1995 | Wilber | |
| 5,912,229 A | 6/1999 | Thim et al. | |
| 6,004,297 A | 12/1999 | Steenfeldt-Jensen | |
| 6,191,021 B1 | 2/2001 | Fuller et al. | |
| 6,191,102 B1 | 2/2001 | DiMarchi et al. | |
| 6,268,343 B1* | 7/2001 | Knudsen et al. | 514/4.8 |
| 6,399,089 B1 | 6/2002 | Yegorova et al. | |
| 6,420,137 B1 | 7/2002 | Strnad et al. | |
| 6,458,924 B2* | 10/2002 | Knudsen et al. | 530/324 |
| 6,844,321 B2 | 1/2005 | Arentsen | |
| 6,939,853 B2 | 9/2005 | Knudsen et al. | |
| 7,235,627 B2 | 6/2007 | Knudson et al. | |
| 8,097,698 B2 | 1/2012 | Knudsen et al. | |
| 2002/0137666 A1* | 9/2002 | Beeley et al. | 514/2 |
| 2002/0187926 A1 | 12/2002 | Knudsen et al. | |
| 2003/0036652 A1* | 2/2003 | Bakthavatchalam et al. | 544/230 |
| 2003/0040469 A1* | 2/2003 | Knudsen | 514/12 |
| 2003/0199672 A1 | 10/2003 | Knudsen et al. | |
| 2003/0232754 A1* | 12/2003 | Holst et al. | 514/12 |
| 2004/0002442 A1 | 1/2004 | Pan et al. | |
| 2004/0106547 A1 | 6/2004 | Larsen et al. | |
| 2007/0161568 A1 | 7/2007 | Holst et al. | |
| 2009/0149387 A1 | 6/2009 | Holst et al. | |
| 2010/0113363 A1 | 5/2010 | Holst et al. | |
| 2011/0028391 A1 | 2/2011 | Holst et al. | |

FOREIGN PATENT DOCUMENTS

| | | |
|---|---|---|
| DK | 1259/96 | 5/1973 |
| EP | 338806 | 2/1994 |
| EP | 0619322 | 10/1994 |
| EP | 897728 | 5/2003 |
| JP | 05-506427 | 9/1993 |
| JP | 07-2695 | 1/1995 |
| JP | 2002-523333 | 7/2002 |
| WO | WO 90/11296 | 10/1990 |
| WO | WO 91/11457 | 8/1991 |
| WO | WO 92/10576 | 6/1992 |
| WO | WO 97/31943 | 9/1997 |
| WO | WO 98/08871 | 3/1998 |
| WO | WO 98/19698 | 5/1998 |
| WO | WO 98/20895 | 5/1998 |
| WO | WO 99/43706 | 9/1999 |
| WO | WO 00/07617 | 2/2000 |
| WO | 00/42026 A1 | 7/2000 |
| WO | 01/57084 A1 | 8/2001 |
| WO | WO 01/72361 | 10/2001 |
| WO | WO 03/002136 | 1/2003 |
| WO | 03/059378 A2 | 7/2003 |
| WO | WO 03/057235 | 7/2003 |
| WO | WO 03/058203 | 7/2003 |
| WO | WO 03/103572 | 12/2003 |
| WO | WO 2004/002556 | 1/2004 |
| WO | 2004/050115 A2 | 6/2004 |
| WO | 2005046716 A1 | 5/2005 |

OTHER PUBLICATIONS

Satia-Abouta et al. ("Energy from Fat Is Associated with Obesity in U.S. Men: Results from the Prostate Cancer Prevention Trial," Preventive Medicine (2002) 34, 493-501).*
Astrup et al. ("Obesity as an adaptation to a high-fat diet: evidence from a cross-sectional study," Am J Clin Nutr (1994) 59, 350-355).*
Kumanyika et al. ("Obesity prevention: the case for action," International Journal of Obesity (2002) 26, 425-436).*
Schrauwen et al. ("The role of high-fat diets and physical activity in the regulation of body weight," British Journal of Nutrition (2000), 84, 417-427).*

(Continued)

Primary Examiner — Christina Bradley
(74) Attorney, Agent, or Firm — Leon Y. Lum

(57) ABSTRACT

GLP-1 agonists selectively decrease the amount of food intake, wherein the food has a high glycemic index or wherein the amount of mono- and di-saccharides together constitute a large proportion of the total amount of carbohydrates.

2 Claims, No Drawings

(56) References Cited

OTHER PUBLICATIONS

Ludwig ("Dietary Glycemic Index and Obesity," J Nutrition (2000) 280S-283S).*
Brand-Miller et al. ("Glycemic index and obesity," American Journal of Clinical Nutrition, (2002) 76(suppl), 281S-5S).*
Ludwig ("The Glycemic Index, Physiological Mechanisms Relating to Obesity, Diabetes, and Cardiovascular Disease," JAMA, (2002), 287, 2414-2423).*
Bouche et al. ("Five-Week, Low—Glycemic Index Diet Decreases Total Fat Mass and Improves Plasma Lipid Profile in Moderately Overweight Nondiabetic Men," Diabetes Care (2002), 25, 822-828).*
Johnson et al. ("Choose Beverages and Foods to Moderate Your Intake of Sugars: The 2000 Dietary Guidelines for Americans—What's All the Fuss About?" J. Nutr. (2001) 131, 2766S-2771S).*
Elliott et al. ("Fructose, weight gain, and the insulin resistance syndrome," Am. J. Clin. Nutr. 2002, 76:911-22).*
www.glycemicindex.com, downloaded Oct. 20, 2014.*
www.caloriecount.about.com, downloaded Oct. 20, 2014.*
Hershey's Miniatures Assortment, www.thehersheycompany.com, downloaded Oct. 20, 2014.*
Brewerton "Binge Eating Disorder" CNS Drugs, 1999, 11(5), 351-361.*
Bjenning & Knudsen, "NN2211, a Protracted GLP-1 Derivative, Potently Reduces Consumption of High-Carbohydrate and High Fat Diets in the Rat", Diabetes Research and Clinical Practice, 2003, vol. 50, pp. 385-386.
Brand-Miller et al., "Glycemic Index and Obesity", Am. J. Clin. Nutr., 2002, vol. 76, pp. 281S-285S.
Ludwig, The Glycemic Index: Physiological Mechanisms Disease Relating to Obesity, Diabetes, and cardiovascular, JAMA, 2002, vol. 287, pp. 2414-2423.
Edwards, C.M.B. et al., Am. J. Physiol. Endocrinol. Metabolism, 2001, vol. 101, Part 1, pp. E155-E161.
Share: Quarterly Update for Inventors from Novo Nordisk, May 2009, vol. 5, Internet: URL:http://www.novonordisk.com/images/investors.
Larsen, P.J. et al., "Systemic Administration of the Long-Acting GLP-1 Derivative NN2211 Induces Lasting and Reversible Weight Loss in Both Normal and Obese Rats", Diabetes, 2001, vol. 50, No. 11 , pp. 2530-2539.
Ahren, B., "Gut Peptides and Type 2 Diabetes Mellitus Treatment," Curr. Diab. Rep., 2003, vol. 3, Part 5, pp. 365-672.
American Diabetes Association, "Consensus Development Conference on Antipsychotic Drugs and Obesity and Diabetes," Diabetes Care (Feb. 2004), 27(2): 596-601.
Baptista, "Body Weight Gain Induced by Antipsychotic Drugs: Mechanisms and Management," Acta Psychiatr. Scand., 1999, 100:3-16.
Bays, "Current and Investigational Antiobesity Agents and Obesity Therapeutic Treatment Targets," Obesity Res., 12: 1197-1211, 2004.
Bell et al., "Exon Duplication and Divergence in the Human Preproglucagon Gene," Nature, Jul. 28, 1983, vol. 304, pp. 368-371.
Bernstein, "Induction of Obesity by Psychotropic Drugs," Annals New York Academy Of Sciences, 1987, 499:203-215.
Bjenning, C.A. et al, "NN2211, a Protracted GLP-1 Derivative, Potently Reduces Consumption of High-Carbohydrate and High-Fat Diets in the Rat," Diabetes Res. Clin. Pract., 2000, vol. 50, Part P1509, pp. S386.
Coccurello et al., "Chronic administration of olanzapine affects Behavioral Satiety Sequence and feeding behavior in female mice," Eat Weight Disord., 2008, 13(3):e55-60.
Flint, A. et al., "Glucagon-like Peptide 1 Promotes Satiety and Suppresses Energy Intake in Humans," J. Clin. Invest., 1998, vol. 101, Part 3, pp. 515-520.
Gendall, K.A. et al., "The Effects of Meal Composition on Subsequent Craving and Binge Eating," Addict Behav., 1999, vol. 24, Part 3, pp. 305-315 (Abstract).

Gothelf et al., "Weight Gain Assoc with Increased Food Intake and Low Habitual Activity Levels in in Male Adolescent Schizophrenic Inpatients Treated with Olanzapine," American Journal of Psychiatry, 2002, vol. 159, No. 6, pp. 1055-1057.
Gregory et al., "Relation Between Gastric Emptying and Short-Term Regulation of Food Intake in the Pig," Physiology and Behavior (1989), vol. 45, pp. 677-683.
Gutniak et al., "Potential Therapeutic Levels of Glucagon-Like Peptide I Achieved in Humans by a Buccal Tablet," Diabetes Care, (1996), vol. 19, pp. 843-848 (Abstract).
Hassan, M. et al., "In Vivo Dynamic Distribution of $^{131}$I-Glucagon-Like Peptide-1 (7-36) Amide in the Rat Studied by Gamma Camera," Nuclear Med. Bio., 1999, vol. 26, pp. 413-420.
Henriksen et al., "Peptide amidation by chemical protein engineering. A combination of enzymic and photochemical synthesis," J. Am. Chem. Soc. (1992), 114(5), 1876-7.
Hirsch J., "The search for new ways to treat obesity," Proc Natl Acad Sci U S A. Jul. 9, 2002;99(14):9096-7.
Horn, W.F. et al., "Effects of Glycemic Index on Hunger, Stress and Arousal," Exp. Biol., 2003, vol. 17, Part 4-5, pp. Ab709.7.
Jandacek and Woods, "Pharmaceutical approaches to the treatment of obesity," Drug Disc Today, 9: 874-880, 2004.
Jensen, P. B. et al., "Transplatable Rat Glucagonomas Cause Acute Onset of Severe Anorexia and Adipsia Despite Highly Elevated NPY mRNA Levels in Hypothalamic Arcuate Nucleus," J. Clin. Inves., 1998, vol. 101, Part 2, pp. 503-510.
Kieffer, T.J. et al., "The Glucagon-Like Peptides," Endocr. Rev., 1999, vol. 20, Part 6, pp. 876-913.
Kinzig, K.P. et al., "The Diverse Roles of Specific GLP-1 Receptors in the Control of Food Intake and the Response to Visceral Illness," J. Neurosci., 2002, vol. 22, Part 23, pp. 10470-10476.
Leadbetter et al., "Clozapine-Induced Weight Gain: Prevalence and Clinical Relevance," Am. J. Psychiatry, 1992, 149:68-72.
Li, He and Mead, "Olanzapine and Risperidone Disrupt Conditioned Avoidance Responding in Phencyclidine-Pretreated or Amphetamine . . . ," Behav. Pharmacol., 2009, 20(1):84-89.
Lykkegaard et al., "The Once-Daily Human GLP-1 Analog, Liraglutide, Reduces Olanzapine-Induced Weight Gain and Glucose Intolerance," Schizophrenia Research, 2008, 103:94-103.
Marx J., "Obesity gene discovery may help solve weighty problem [news]." SCIENCE, (Dec. 2, 1994) 266 (5190) 1477-8.
McIntyre et al., "Mechanisms of Antipsychotic-Induced Weight Gain," J Clin Psychiatry; 2001, 62(Suppl 23):23-29.
McMahon, L.R. et al., "PVN Infusion of GLP-1-(7-36) Amide Suppresses Feeding But Does Not Induce Aversion or Alter Locomotion in Rats," Am. J. Physiol., 1998, vol. 274, pp. R23-R29.
Meeran, K. et al., "Repeated Intracerebroventricular Administration of Glucagon-Like Peptide-1-(7-36) Amide or Exendin-(9-39) Alters Body Weight in the Rat," Endocrinology, 1999, vol. 140, part 1, pp. 244-250.
Meier, J.J. et al., "Glucagon-Like Peptide 1 as a Regulator of Food Intake and Body Weight: Therapeutic Perspectives," Euro. J. Pharmacol., 2002, vol. 440, Part 2-3, pp. 269-279.
Nauck, M.A. et al., "Normalization of Fasting Hyperglycaemia by Exogenous Glucagon-Like Peptide 1 (7-36 Amide) in Type 2 (Non-Insulin-Dependent) Diabetic Patients," Diabetolgia, 1993, vol. 36, pp. 741-744.
Navarro et al., "Colocalization of Glucagon-Like Peptide-1 (GLP-1) Receptors, Glucose Transporter GLUT-2, and Glucokinase . . . ," Journal of Neurochemistry, vol. 67, pp. 1982-1991 (1996).
Ole Nordfang, Minutes from EASD Meeting, Vienna, Sep. 1996.
Opinions of the Lords of Appeal for Judgement in the cause *Conor Medsystems Incorporated* v. *Angiotech Pharmaceuticals Incorporated*, [2008] UKHL 49.
Orskov et al., "All Products of Proglucagon are Elevated in Plasma from Uremic Patients," Journal of Clinical Endocrinology and Metabolism (1992), vol. 74, No. 2, pp. 379-384.
Procyshyn, Chau and Tse, "Clozapine's Effects on Body Weight and Resting Metabolic Rate: A Case Series," Schizophr Res., 2004, 66(2-3):159-62.
Raun, K. et al., "Liraglutide, a Long-Acting Glucagon-Like Peptide-1 Analog, Reduces Body Weight and Food Intake in Obese

(56) References Cited

OTHER PUBLICATIONS

Candy-Fed Rats, Whereas a Dipeptidyl Peptidase-IV Inhibitor, Vildagliptin, Does Not", Diabetes, 2007, vol. 56, No. 1, pp. 8-15.
Raun, K. et al., "The GLP-1 Derivative NN2211 Normalizes Food Intake and Lowers Body Weight in a Hyperphagic Minipig Model,". Diabetes, 2003, vol. 52, p. A325.
Rink T J., "In search of a satiety factor," NATURE,(Dec. 1, 1994)372(6505) 406-7.
Robinson et al., "Gastric Control of Food Intake," Journal of Psychosomatic Research (1988), vol. 32, No. 6, pp. 593-606.
Rodriguez De Fonseca, F. et al., "Peripheral Versus Central Effects of Glucagon-Like Peptide-1 Receptor Agonists on Satiety and Body Weight Loss in Zucker Obese Rats," Metabolism, 2000, vol. 49, Part 6, pp. 709-717.
Sentissi et al., "Impact of Antipsychotic Treatments on the Motivation to Eat: Preliminary Results in 153 Schizophrenic Patients," Int. Clin. Psychopharmacol., 2009, 24(5):257-64.
Sturis, et al., "GLP-1 Derivative Liraglutide in Rats with β-Cell Deficiencies: Influence of Metabolic State on β-Cell Mass Dynamics", British Journal of Pharmacology, 2003, vol. 140, No. 1, pp. 123-132.
Suzuki et al., "Comparison of the effects of various C-terminal and N- Terminal fragment peptides of glucagon-like peptide-1 on insulin and glucagon release from the isolated perfused rat pancreas," Endocrinology, (Dec. 1989) 125(6) 3109-14.
Tang-Christensen, M. et al., "Glucagon-Like Peptide 1(7-36) Amide's Central Inhibition of Feeding and Peripheral Inhibition of Drinking are Abolished by Neonatal Monosodium Glutamate Treatment," Diabetes, 1998, vol. 47, pp. 530-537.
Thorens T., "Glucagon-like peptide-1 and control of insulin secretion," Diabete & Metabolisme (Paris). 1995,21, 311-318.
Turton, M.D. et al., "A Role for Glucagon-Like Peptide-1 in the Central Regulation of Feeding," Nature, 1996, vol. 379, pp. 69-72.
U.S. Appl. No. 60/030,213, filed Nov. 5, 1996 by DiMarchi.
Van Dijk, G. et al., "Glucagon-Like Peptide-1 (7-36) Amide: a Central Regulator of Satiety and Interoceptive Stress," Neuropeptides, 1999, vol. 33, Part 3, pp. 406-414.
Wang et al., "Glucagon-like peptide-1 is a physiological incretin in rat," J. Clin, Invest.,(Jan. 1995)95(1) 417-21.
Wettergren et al., "Truncated GLP-1 (proglucagon 78-107-amide) inhibits Gastric and pancreatic functions in man," Digest. Dis. Sci., (Apr. 1993) 38(4) 665-73.
Wettergren, A. et al., "Glucagon-Like Peptide-1 Inhibits Gastropancreatic Function by Inhibiting Central Parasympathetic Outflow," Am. J. Physiol., 1998, vol. 275, pp. G984-G992 (Abstract).
Whitcomb, D.C. et al., "Characterization of Saturable Binding Sites for Circulating Pancreatic Polypeptide in Rat Brain," Am. J. Physiol., 1990, vol. 259, pp. G687-G691.
Woods et al., "Signals that regulate food intake and energy homeostasis," Science, 280:1378-1383, May 29, 1998.
Wurtman, J. et al., Dexfenfluramine, Fluoxetine, and Weight Loss Among Female Carbohydrate Cravers, Neuropsychopharmacology, 1993, vol. 9, Part 3, pp. 201-210.
Young et al., "Dose-Responses for the Slowing of Gastric Emptying in a Rodent Model by Glucagon-Like Peptide (7-36)NH2, Amylin, Cholecystokinin, and Other Possible Regulators of Nutrient Uptake," Metabolism: Clinical and Experimental (1996), vol. 45, No. 1, pp. 1-3.
Zander, M. et al., "Effect of 6-Week Course of Glucagon-Like Peptide 1 on Glycaemic Control, Insulin Sensitivity, and β-Cell Function in Type 2 Diabetes: a Parallel-Group Study," The Lancet, 2002, vol. 359, pp. 824-830.
Zhang et al., "Positional cloning of the mouse obese gene and its human homologue," NATURE, (Dec. 1, 1994)372(6505)425-32.
Zimmermann et al., "Epidemiology, Implications and Mechanisms Underlying Drug-Induced Weight Gain in Psychiatric Patients," J. Psych. Res., 37: 193-220, 2003.
Non-Final Office Action mailed Oct. 5, 2006 in U.S. Appl. No. 10/382,438, filed Mar. 6, 2003 by Holst et al.
Non-Final Office Action mailed Sep. 12, 2008 in U.S. Appl. No. 11/714,000, filed Mar. 5, 2007 by Holst et al.
Non-Final Office Action mailed Sep. 1, 2009 in U.S. Appl. No. 12/370,308, filed Feb. 12, 2009 by Holst et al.
Non-Final Office Action mailed Jun. 23, 2010 in U.S. Appl. No. 12/651,685, filed Jan. 4, 2010 by Holst et al.
Non-Final Office Action mailed Apr. 1, 2011 in U.S. Appl. No. 12/905,324, filed Oct. 15, 2010 by Holst et al.
Non-Final Office Action mailed Sep. 12, 2007 in U.S. Appl. No. 11/448,545, filed Jun. 7, 2006 by Raun et al.
Final Office Action mailed Apr. 3, 2008 in U.S. Appl. No. 11/448,545, filed Jun. 7, 2006 by Raun et al.
Non-Final Office Action mailed Jan. 27, 2009 in U.S. Appl. No. 11/448,545, filed Jun. 7, 2006 by Raun et al.
Non-Final Office Action mailed Nov. 12, 2009 in U.S. Appl. No. 11/448,545, filed Jun. 7, 2006 by Raun et al.
Non-Final Office Action mailed Jun. 10, 2010 in U.S. Appl. No. 11/629,238, filed Oct. 11, 2006 by Bock et al.
Final Office Action mailed Dec. 28, 2010 in U.S. Appl. No. 11/629,238, filed Oct. 11, 2006 by Bock et al.
U.S. Appl. No. 13/249,799, filed Sep. 30, 2011, by Holst et al.
U.S. Appl. No. 09/723,551, filed Nov. 28, 2000, by Holst et al.
U.S. Appl. No. 08/965,135, filed Nov. 6, 1997, by Holst et al.
Case et al., 2010, "The Potential Role of Appetite in Predicting Weight Changes During Treatment With Olanzapine", BMC Psychiatry., 10(72): pp. 1-9.
Tang-Christensen, M. et al., "Central Administration of GLP-1-(7-36) Amide Inhibits Food and Water Intake in Rats" American Journal of Physiology, 1996, vol. 271, (40R), pp. 848-856.
U.S. Appl. No. 60/030,213, Richard D. DiMarchi.
C.B. Juhl "Bedtime Administration of NN2211, a Long-Acting GLP-1 Derivative, Substantially Reduces Fasting and Postprandial Glycemia in Type 2 Diabetes." Diabetes vol. 51:2: 424-429 (2002).
Peters, et al. "A glucagon-like receptor agonist and an antagonist modify macronutrient selection by rats." The Journal of Nutrition vol. 131(8): 2164-2170 (2001).
Stephen C Woods et al. "Signal that Regulates Food Intake and Energy" Science. 1998 vol. 280 pp. 1378-1383.
Zhang et al. "Positional Cloning of the Mouse Obese Gene and Its" Nature 1994 vol. 372 pp. 425-432.
Jean Marx. "Obesity Gene Discovery May Help Solve Weighty" Science. 1994 vol. 266 pp. 1477-1478.
Hagan et al., "A New Animal Model of Binge Eating: Key Synergistic Role of Past Calorie Restriction and Stress," Physiology & Behavior, 2002, vol. 77, pp. 45-54.
Avena et al., "A Diet Promoting Sugar Dependency Causes Behavioral Cross-Sensitization to a Low Dose of Ampetamine," Neuroscience, 2003, vol. 122, pp. 17-20.
Dickson et al., "The Glucagon-Like Peptide 1 (GLP-1) Analogue, Exendin-4, Decreases the Rewarding Value of Food: A New Role for Mesolimbic GLP-1 Receptors," The Journal of Neuroscience, 2012, vol. 32, No. 14, pp. 4812-4820.
Dingemans AE et al. Binge eating disorder: a review, International Journal Of Obesity,2002, pp. 299-307, URL: http://search.proquest.com/docview/219244142.

\* cited by examiner

REGULATION OF FOOD PREFERENCE USING GLP-1 AGONISTS

CROSS-REFERENCE TO RELATED APPLICATIONS

This application is a continuation of U.S. application Ser. No. 11/448,545, filed Jun. 7, 2006, which is a continuation of International Application Number PCT/DK2004/000853, filed Dec. 9, 2004, which claims priority to Danish Patent Application Number PA 2003 01816, filed Dec. 9, 2003, and U.S. Provisional Application No. 60/529,480, filed Dec. 15, 2003, the contents of each of which is incorporated herein in its entirety.

FIELD OF THE INVENTION

The present invention relates to the use of GLP-1 agonists to reduce calorie intake from foods with a high glycemic index, or from foods wherein a high proportion of the carbohydrates is constituted by mono- and di-saccharides.

BACKGROUND OF THE INVENTION

Lifestyle in many parts of the world today is characterized by an enormous meal and "between-meal" intake of calories from solid food and snacks as well as drinkable calories. This lifestyle is often referred to as "western world lifestyle", and it is generally regarded as unhealthy. Our food earlier consisted of an average of 10% protein, 30% fat and 60% carbohydrates; the carbohydrates mostly in the form of slowly absorbed carbohydrates. The food and especially the between-meal snack consumed today often has a much higher amount of quickly absorbed carbohydrates and fat. The amount of quickly absorbed carbohydrates may be measured as the glycemic index or as the fraction of mono- and di-saccharide of the total amount of carbohydrates. The excess intake of quickly absorbed carbohydrates and/or high fat leads to reduced feelings of hunger, and to increased stress (W F Horn, N Keim. Effects of glycemic index on hunger, stress and arousral. FASEB Journal 2003:17(4-5): A7097). Also, some human beings have cravings for sweet and/or fat food, sometimes enhanced by stress or premenstrual tension, or they may have psychological problems manifested as binge eating or compulsive eating habits. As a consequence of this western world lifestyle and the psychological disorders described above there is a general excessive intake of food like sodas, juice, chocolate milk, sweetened coffee, candy, chocolate, cake, biscuits, crackers, french fries, burgers, white bread with jam or jelly or honey, chips, sweet and fat cereals.

GLP-1 has been described as an incretin hormone with a large array of effects. GLP-1 was discovered in 1984 and found to be an important incretin [Nauck, M. A.; Kleine, N.; Orskov, C.; Hoist, J. J.; Willms, B.; Creutzfeldt, W., *Diabetologia* 1993, 36, 741-744]. It is released from the L-cells in the intestine upon a meal and potently releases insulin from the beta-cells in the pancreas. Numerous effects other than just stimulation of insulin release have been ascribed to GLP-1. In the pancreas, GLP-1 not only releases insulin, it does so in a glucose-dependent manner, and it has a number of other functionally important effects: stimulation of insulin biosynthesis, restoration of glucose sensitivity to the islets, stimulation of increased expression of the glucose transporter GLUT-2 and glucokinase. [4,5,6] GLP-1 also has a number of effects on regulation of beta-cell mass, stimulation of replication and growth of existing beta-cells, inhibition of apoptosis and neogenesis of new b-cells from duct precursor cells, which leads to reduced hepatic glucose output. In the gut, GLP-1 is a potent inhibitor of motility and gastric emptying and has also been shown to inhibit gastric acid secretion. The inhibition of gastric emptying leads to decreased food intake and reduced body weight [Flint, A.; Raben, A.; Astrup, A.; Hoist, J. J., *J Clin Inv* 1998, 101, 515-520; Zander, M.; Madsbad, S.; Madsen, J. L.; Hoist, J. J., *Lancet* 2002, 359, 824-830][11,12]. Thus, the current belief is that the GLP-1 agonists may be able to control the progression of the type 2 diabetes disease by not only controlling blood glucose, but also by a number of other effects. GLP-1 has also been proposed to have direct effects on glucose uptake in liver, muscle and adipose tissue but the quantitative significance of these effects has been questioned [Kieffer, T. J.; Habener, J. F., *Endocrine Reviews* 1999, 20, 876-913]. New publications even suggest that it does not stop here, there may be specific receptors in the heart which along with the benefits of reducing blood glucose may prevent cardiovascular complications, and that GLP-1 stimulates memory and learning capabilities. A comprehensive review exists on the glucagon-like peptides [Kieffer, T. J.; Habener, J. F., *Endocrine Reviews* 1999, 20, 876-9139.

A large number of articles have been published on the effects of GLP-1 on food intake. GLP-1 reduces food intake, both after central administration and after peripheral administration (Turton, Nature 196:379; 69-72, Flint *J Clin Inv* 1998, 101, 515-520). Also, central administration of high doses of GLP-1 induces taste aversion (Tang-Christensen, Diabetes 1998:47:530-537). However, site directed micro injections of GLP-1 into the PVN induces pharmacologically specific inhibition of feeding without induction of taste aversive behaviour (McMahon, Wellman, Am. J. Phys 1998: 274, R23-R29). In animals having their arcuate nucleus lesioned by neonatal monosodium glutamate treatment, central administration of GLP-1 has lost its anorectic potential but is still inducing taste aversion (Tang-Christensen, Diabetes 1998:47:530-537). Further support of dissociated specific satiety inducing central targets of GLP-1 and non-specific taste aversion inducing central targets come from lesion studies showing that PVN constitute a target where GLP-1 elicits satiety whereas the central amygdala and the parabrachial nuclei constitute areas involved in mediating GLP-1 induced taste aversion (van Dijk and Thiele, Neuropeptides 1999: 33, 406-414). Other studies have confirmed that there are diverse roles of GLP-1 receptors in the control of food intake and taste aversion (Kinzig, J Neuroscience 2002:22(23): 10470-10476). Also, chronic repetitive central administration of the GLP-1 antagonist, exendin-9-39, enhances food intake suggesting that an endogenous tone of satiety mediating GLP-1 exists in central pathways mediating body weight homeostasis (Meeran, Endocrinology 199: 140:244-250). In a human study, continuous infusion of GLP-1 to type 2 diabetic patients gave rise to marked improvement of glycaemic control and caused moderate yet non-significant weight loss (Zander, Lancet 2002: 359, 824-830). The site of the anorectic action of peripherally administered GLP-1 is unknown but participation of both central and peripheral sites in GLP-1 are likely, because a recent study has shown that radiolabelled GLP-1 readily gains access to the central nervous system (Hassan, Nucl Med Biol 1999:26:413-420). The nucleus of the solitary tract is situated adjacent to the blood brain barrier free area postrema, and other studies using radio-labelled neuropeptides have shown that peripheral administration of neuropeptides gain access both to the area postrema as well as the adjacent subpostreme regions including the dorsal vagal complex (Whitcomb Am J Phys 1990: 259:G687-G691). Thus, it is likely that peripherally administered GLP-1 enters the nucleus of the solitary tract with resulting impact on ascending neurones involved in regulation of food intake. Interaction of GLP-1 with vagal afferents from the gastrointestinal tract should also be considered as mediator of its anorectic actions because transection of the vagus nerve renders the stomach of anaesthetised pigs insensitive to the akinetic actions of intravenously administered GLP-1 (Wettergren, Am J Phys 1998:275:984-992). Probably both vagal afferents and GLP-1 receptors accessible from the periphery are responsible for the anorexia induced by GLP-1, because we have seen that bilateral subdiaphragmatic vagotomy on rats carrying the anorectic GLP-1 producing tumour has no impact on the development of anorexia (Jensen, JCI 1998: 101:503-510). Last, GLP-1 has been shown to inhibit intake of different kinds of food, both rich in fat and in carbohydrate (Bjenning, Diabetes Res and Clin Prac 2000:50(1): S386).

Despite this in-dept knowledge it as never been described that a GLP-1 agonist has the effect of specifically modifying the intake of food associated with an unhealthy western world lifestyle. This effect could be useful in the treatment of all kinds of disorders linked to an increased intake of sweet or fat food.

Earlier studies suggest that seretoninergic drugs effect a selective reduction in the intake of carbohydrate rich food [Wurthman, Neurophsycopharmacology, 1993, 9, 201-210].

SUMMARY OF THE INVENTION

The present inventors have surprisingly found that GLP-1 agonists can be used to specifically modify the intake of food by a subject, wherein said food has a high glycemic index or food wherein mono- or di-saccharide constitute a large proportion of the total amount of carbohydrate. Accordingly, in one aspect the present invention relates to a method for reducing intake of food by a subject, wherein said food has a glycemic index above 60%, or wherein said food has a glycemic index above 40% combined with that more than 30% of the total amount of energy stems from fat, said method comprising administering to said subject an effective amount of a GLP-1 agonist.

In another aspect, the invention relates to a method for reducing intake of food by a subject, wherein mono- and di-saccharides in said food together constitute more than 25% of the total amount of carbohydrate in said food, said method comprising administering to said subject an effective amount of a GLP-1 agonist.

In another aspect, the invention relates to a method of increasing intake of food in a subject, wherein said food has a glycemic index below 60%, or wherein said food has a glycemic index below 40% combined with that less than 30% of the total amount of energy stems from fat, said method comprising administering to said subject an effective amount of a GLP-1 agonist.

In still another aspect, the invention relates to a method of increasing intake of food in a subject wherein mono- and di-saccharides together constitute less than 25% of the total amount of carbohydrate in said food, said method comprising administering to said subject an effective amount of a GLP-1 agonist.

In still another aspect, the invention relates to a method of treating a subject with an abnormal or excessive intake of food wherein the glycemic index is above 60%, or wherein the glycemic index is above 40% combined with that more than 30% of the total amount of energy stems from fat, said method comprising administering to said subject an effective amount of a GLP-1 agonist.

In still another aspect, the invention relates to a method of treating a subject with an abnormal or excessive intake of food wherein the mono- and di-saccharides together constitute more than 25% of the total amount of carbohydrates, said method comprising administering to said subject an effective amount of a GLP-1 agonist.

In yet another aspect, the invention relates to a method for promoting the sales of a GLP-1 agonist-containing product, said method comprising the public distribution of information describing the reduced intake of food with a high glycemic index or food wherein mono- and di-saccharides together constitute a large proportion of the total amount of carbohydrates attributable to the consumption of said product and optionally the benefits connected with that.

In yet another aspect, the invention relates to a pharmaceutical product, comprising: (a) a GLP-1 agonist which reduces the intake of food with a high glycemic index or food wherein mono- and di-saccharides together constitute a large proportion of the total amount of carbohydrates in a container; and (b) a notice associated with said container in a form prescribed by a governmental agency regulating the manufacture, use, or sale of pharmaceuticals, which notice is reflective of approval by said agency of said GLP-1 compound for human or veterinary administration to reduce intake of food with a high glycemic index.

DEFINITIONS

The glycemic index is a measure of the ability of food to raise the blood glucose level. The glycemic index of a food is determined by feeding a group consisting of at least 10 healthy people a portion of food containing 50 grams of digestible (available) carbohydrate and then measure the effect on their blood glucose levels during the following two hours. For each person, the area under their two-hour blood glucose response (glucose AUC) is measured. On another occasion, the same group of people consume 50 g of glucose, and their two-hour blood glucose response is also measured. The glycemic index for the food is the AUC determined for the food divided by the AUC determined for glucose multiplied by 100% (calculated as the average for the group). Food with a high glycemic index contain rapidly digested carbohydrate, which produces a large rapid rise and fall in the level of blood glucose. In contrast, foods with a low glycemic index score contain slowly digested carbohydrate, which produces a gradual, relatively low rise in the level of blood glucose.

In the present context "mono-saccharides" is intended to indicate a carbohydrate that cannot be hydrolysed to simpler carbohydrates. The most relevant mono-saccharides in food are glucose and fructose.

In the present context "di-saccharides" is intended to indicate carbohydrates which can be hydrolysed into two mono-saccharides. The most relevant di-saccharides in food are sucrose, maltose and lactose.

The amount of mono- and di-saccharides in food may be analysed specifically by enzymatic, gas-liquid chromatography (GLC) or high performance liquid chromatography (HPLC) methods. Depending on the food matrix to be analyzed, extraction of the low molecular weight carbohydrates in aqueous ethanol, usually 80% (v/v), may be advisable before analysis. Relevant analysis methods are provided in e.g. Southgate, "Determination of food carbohydrates", Elsevier, Science Publishers, Barkinggate, 1991;

Greenfield, "Food composition data. Production, management and use", Elsevier Appleid Science, London, 1992; and Department of Health, "Dietery sugars and human health, Her Majesty's Stationary Office, London, 1989.

In the present context, "carbohydrates" are defined as in "Carbohydrates in human nutrition. (FAO Food and Nutrition Paper-66)", Report of a Joint FAO/WHO Expert Consultation, Rome, 14-18 Apr. 1997, Report of a Joint FAO/WHO Expert Consultation Rome, 14-18 Apr. 1997, namely as polyhydroxy aldehydes, ketones, alcohols, acids, their simple derivatives and their polymers having linkages of the acetal type.

In the present context, "fat" is intended to indicate mono-, di- and tri-carboxylic acid ester derived from glycerol and cholesterol, where the glycerols are the more important source of energy in the food of the two. The amount of fat in food may be determined as disclosed in FAO: Food energy—methods of analysis and conversion factors, Report of a Technical Workshop, Rome, 3-6 Dec. 2002.

In the present context, "total carbohydrate content" is intended to indicate the sum of carbohydrates present in the food. It is not measured as such, but rather calculated as the difference between the total weight of the food and the sum of the weights of the non-carbohydrate components [FAO: Food energy—methods of analysis and conversion factors, Report of a Technical Workshop, Rome, 3-6 Dec. 2002.

In the present context "obese" or "obesity" implies an excess of adipose tissue. In this context obesity is best viewed as any degree of excess adiposity that imparts a health risk. The distinction between normal and obese individuals can only be approximated, but the health risk imparted by obesity is probably a continuum with increasing adiposity. However, in the context of the present invention, individuals with a body mass index (BMI=body weight in kilograms divided by the square of the height in meters) above 25 are to be regarded as obese.

In the present context "food", unless otherwise stated, is intended to indicate food in any form, i.e. both liquid and solid food, as well as basic food and candy, snacks, etc.

In the present context, "abnormal or excessive intake of food" is intended to indicate an intake with pathological consequences, such as obesity, or which can be ascribed to a psychological state connected with e.g. pregnancy or premenstrual tension, or to a psychological disease, such as binge eating or compulsory eating habits.

An "effective amount" of a compound as used herein means an amount sufficient to cure, alleviate or partially arrest the clinical manifestations of a given disease or state and its complications. An amount adequate to accomplish this is defined as "effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications.

In the present context "reducing intake of food" is intended to indicate that the amount of food (measured by its energy content) eaten by a group consisting of one or more subjects being administered a GLP-1 agonist is reduced compared to a similar control group not being administered a GLP-1 agonist, as provided in the present invention. Similarly, "increasing intake of food" is intended to indicate that the amount of food (measured by its energy content) eaten by a group consisting of one or more subjects being administered a GLP-1 agonist is increased compared to a similar control group not being administered a GLP-1 agonist, as provided in the present invention.

DESCRIPTION OF THE INVENTION

In one embodiment, the present invention relates to the use of GLP-1 agonists to modify the intake of specific types of food by a subject wherein the food has a high glycemic index or wherein the mono- and di-saccharides together constitute a large proportion of the total amount of carbohydrate in said food.

In one embodiment, the invention provides a method for decreasing the intake of food by a subject, wherein the food has a high glycemic index or wherein the mono- and di-saccharides together constitute a large proportion of the total amount of carbohydrate in said food, said method comprising the administration of an effective amount of a GLP-1 agonist to said subject. In particular, the glycemic index of the food may be above 60%, such as above 65%, such as above 70%, such as above 75%, such as above 80%, such as above 90%.

In another embodiment, the invention provides a method for decreasing the intake of food by a subject, wherein the food has a glycemic index above 40%, and wherein more than 30% of the total amount of energy stems from fat, the method comprising administering an effective amount of a GLP-1 agonist to said subject. This embodiment includes any combination of food with a glycemic index above 40%, such as above 45%, such as above 50%, such as above 55%, such as above 60%, such as above 65%, such as above 70%, such as above 75%, such as above 80%, such as above 90% and wherein more than 30%, such as more than 35%, such as more than 40%, such as more than 50%, such as more than 60%, such as more than 70%, such as more than 80% of the total amount of energy stems from fat.

In one embodiment, the invention provides a method of decreasing the intake of food by a subject, wherein mono- and di-saccharides together constitute more than 25% of the total amount of carbohydrate in said food, the method comprising administering to said subject an effective amount of a GLP-1 agonist. In particular mono- and di-saccharides together constitute more than 30%, such as more than 35%, such as more than 40%, such as more than 45%, such as more than 50%, such as more than 70%, such as more than 80%, such as more than 90%, or even 100%. In particular, more than 30%, such as more than 40%, such as more than 50%, such as more than 60%, such as more than 70%, such as more than 80% of the total amount of energy in said food stems from fat. In one embodiment, more than 25% of the mono- di- and tri-saccharides together constitute more than 25% of the total amount of carbohydrates.

In another embodiment, the invention provides a method of increasing the intake of food by a subject, wherein the food has a low glycemic index or wherein the mono- and di-saccharides together constitute a small proportion of the total amount of carbohydrate in said food, said method comprising the administration of an effective amount of a GLP-1 agonist to said subject. In particular the glycemic index of the food may be below 60%, such as below 50%, such as below 40%, such as below 35%, such as below 30%, such as below 20%, such as below 10%, such as below 5%.

In another embodiment, the invention provides a method of increasing the intake of food by a subject wherein the food has a glycemic index below 40%, and wherein less than 30% of the total amount of energy stems from fat, said method comprising the administration to a subject of an effective amount of a GLP-1 agonist. This embodiment includes any combination of food with a glycemic index below 40%, such as below 30%, such as below 20%, such as below 10%, such as below 5% and wherein less than 30%, such as less than 20%, such as less than 10%, such as less than 5% of the total amount of energy stems from fat.

In yet another embodiment, the invention provides a method of increasing the intake of food by a subject, wherein mono- and di-saccharides together constitute less than 25% of the total amount of carbohydrates in said food, such as less than 20%, such as less that 15%, such as less than 10%. In particular, the food is also poor in fat as measured by how much of the total amount of energy in the food stems from fat. In particular less than 30%, such as less than 25%, such as less than 20%, such as less than 15%, such as less than 10%, or even less than 5% of the total energy stems from fat. In another embodiment, mono-, di- and tri-saccharides together constitutes less than 25% of the total amount of carbohydrates.

In another embodiment, the decrease in intake of food with a high glycemic index or food wherein mono- and di-saccharides together constitute a large proportion of the total amount of carbohydrates, as discussed above, is accompanied by an increase in the intake of food with a low glycemic index or of food wherein mono- and di-saccharides together constitute as small proportion of the total amount of carbohydrates, as discussed above.

The amount of energy in food is typically quoted in calories or joules, and it can be measured by burning the food, e.g. in a bomb calorimeter. The amount of energy attributable to fat can be determined by multiplying the amount of fat in the food, analysed as discussed above, with 38 kJ/g.

It is well-known that many people prefer sweet and/or fatty food because they think it has a better taste. Accordingly, the present invention also provides a method a regulating taste preferences, and in particular regulating taste preferences away from sweet and fatty food, said method comprising the administration of an effective amount of a GLP-1 agonist.

It is quite clear that the western world life style is not healthy as evidenced by the increase in obesity with all its pathological consequences, such as diabetes and cardiovascular complications, and in that sense the life style must be regarded as abnormal. Accordingly, in one embodiment, the present invention relates to a method of normalising lifestyle, and in particular the food preference, said method comprising the administration of an effective amount of a GLP-1 agonist.

In one embodiment, the subject to be treated has an increased appetite, hunger or craving for sweet or fat food. This may be related to e.g. stress, quit of smoking, pregnancy, premenstrual tension, or it can be ascribed physiological problems or diseases, such as binge eating, compulsive eating habits and Seasonal Affective Disorder.

Binge eating disorder (BED) is a fairly new diagnosable disorder—see e.g. *Int. J. Obesity,* 2002, 26, 299-307 and *Curr. Opin. Pshyciatry,* 17, 43-48, 2004. BED is characterised by binge eating episodes as is bulimia nervosa (BN). However, subjects with BED do not, contrary to patients with BN, engage in compensatory behaviours, such as e.g. self-induced vomiting, excessive exercise, and misuse of laxatives, diuretics or enemas. Studies have shown that 1-3% of the general population suffer from BED, whereas a higher prevalence (up to 25-30%) have been reported for obese patients [*Int. J. Obesity,* 2002, 26, 299-307]. These numbers show that BED subjects may or may not be obese, and that obese patients may or may not have BED, i.e. that the cause of the obesity is BED. However, a proportion of subjects with BED eventually becomes obese due to the excess calorie intake. Laboratory studies have shown that BED patients consumed more dessert and snack (rich in fat and poor in proteins) than did an obese control group [*Int. J. Obesity,* 2002, 26, 299-307], and the method of the present invention is thus believed to be particular well-suited for treatment of BED.

In one embodiment, the invention relates to a method or treating BED in a subject, the method comprising administering to said subject an effective amount of a GLP-1 agonist. In particular, said subject is obese.

In one embodiment, the invention relates to the use of a GLP-1 agonist in the manufacture of a medicament for the treatment of BED in a subject. In particular, said subject is obese.

Bulimia nervosa is characterised by the same binge eating episodes as is BED, however, BN is, however, also characterised by the above mentioned compensatory behaviour. A proportion of subjects with BN will eventually become obese to the extent that the compensatory behaviour cannot fully compensate the excess calorie intake. Studies have compared binges of patients with BN and with BED concluding that binges in subjects with BN were higher in carbohydrates and sugar content than those of subjects with BED. No difference was, however, found in the number of consumed calories [*Int. J. Obesity,* 2002, 26, 299-307]. The methods of the present invention is therefore believed to be particular well-suited for the treatment of BN.

In one embodiment, the invention relates to a method of treating BN in a subject, the method comprising administering to said subject an effective amount of a GLP-1 agonist. In particular, said subject is obese.

In one embodiment, the invention relates to the use of a GLP-1 agonist in the manufacture of a medicament for the treatment of BN in a subject. In particular, said subject is obese.

Craving for food or the intense desire to eat a particular food is normally associated with energy dense food, such as fatty or carbohydrate-rich food [*Appetite,* 17, 177-185, 1991; *Appetite,* 17, 167-175, 1991]. Examples of such foods include chocolate, biscuits, cakes and snacks. A proportion of food cravers eventually become obese due to the excess calorie intake. The methods of the present invention are believed to be particular well-suited for the treatment of food craving, in particular craving for fatty or carbohydrate-rich food.

In one embodiment, the invention relates to a method of treating food craving, such as craving for fatty or carbohydrate-rich food, such as chocolate craving in a subject, the method comprising administering to said subject an effective amount of a GLP-1 agonist.

A snack is typically a light, casual, hurried convenience meal eaten between real meals. Snacks are typically fatty and carbohydrate-rich. Studies have shown that there is an increasing prevalence of snacking, especially among US children, and that snacking is a significant cause for the increase in BMI in e.g children [*J. Pediatrics,* 138, 493-498, 2001; *Obes. Res.,* 11, 143-151, 2003]. A shift towards more healthy snacks could probably arrest or change the increase in BMI which has taken place over the last years. Data in shown here illustrate that GLP-1 agonists are capable of shifting food preferences from fatty and carbohydrate-rich food to low-fat glycemic index low food. GLP-1 agonist are therefore useful in diminishing the amount of snacking or in changing the preference of snack to more healthy snack.

In one embodiment, the invention provides a method of changing the snack preference in a subject to low fat, glycemic index low snack, the method comprising administration of an effective amount of a GLP-1 agonist to said subject. In particular, said subject is obese.

In one embodiment, the invention provides a method of lowering the amount a snack intake ("snacking") of a subject, the method comprising administering to said subject an effective amount of a GLP-1 agonist. In particular, said subject is obese.

According to the above discussion, GLP-1 agonists are believed to be particular useful in the treatment of obesity, wherein the obesity is caused by BED, BN, food craving (in particular chocolate craving) or snacking.

The subject of the present invention can in principle be any animal with GLP-1 receptors, and in particular mammals, such as humans, pet animals, such as cats and dogs, and zoo animals, such as elephants, giraffes, lions and snakes.

In another embodiment, the invention relates to a method of promoting sales, purchase, buying or trade of a GLP-1 agonist-containing product, said method comprising the public distribution of information describing the reduced intake of food with a high glycemic index or food wherein mono- and di-saccharides together constitute a large proportion of the total amount of carbohydrates attributable to the consumption of said product and the benefits connected with that, an in particular the health benefits. In particular, said distribution of said information is achieved by a method selected from the group consisting of verbal communication, pamphlet distribution, print media, audio tapes, magnetic media, digital media, audiovisual media, billboards, advertising, newspapers, magazines, direct mailings, radio, television, electronic mail, braille, electronic media, banner ads, fiber optics, and laser light shows. In particular, said product is a pharmaceutical product.

In one embodiment of the methods of the present invention, the GLP-1 agonist is administered to the subject in connection with a meal. In the present context, "in connection with a meal" is intended to indicate a period of up to four hours before or after the meal, such as up to 3 hours before or after, such as up to 2 hours before or after, such as up to 1 hour before or after, such as 30 minutes before or after, such as 15 minutes before or after, such directly in connection with the meal.

In the present context, "a GLP-1 agonist" is understood to refer to any compound, including peptides and non-peptide compounds, which fully or partially activate the human GLP-1 receptor. In a preferred embodiment, the "GLP-1 agonist" is any peptide or non-peptide small molecule that binds to a GLP-1 receptor, preferably with an affinity constant ($K_D$) or a potency ($EC_{50}$) of below 1 µM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 agonist may be administered to an animal and the insulin concentration measured over time.

In one embodiment, the GLP-1 agonist is selected from the group consisting of GLP-1(7-36)-amide, GLP-1(7-37), a GLP-1(7-36)-amide analogue, a GLP-1(7-37) analogue, or a derivative of any of these.

In the present application, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both. Typically "an analogue" is a peptide wherein 6 or less amino acids have been substituted and/or added and/or deleted from the parent peptide, more preferably a peptide wherein 3 or less amino acids have been substituted and/or added and/or deleted from the parent peptide, and most preferably, a peptide wherein one amino acid has been substituted and/or added and/or deleted from the parent peptide.

In the present application, "a derivative" is used to designate a peptide or analogue thereof which is chemically modified by introducing e.g. ester, alkyl or lipophilic functionalities on one or more amino acid residues of the peptide or analogue thereof. Methods for identifying GLP-1 agonists are described in WO 93/19175 (Novo Nordisk A/S) and examples of suitable GLP-1 analogues and derivatives which can be used according to the present invention includes those referred to in WO 99/43705 (Novo Nordisk A/S), WO 99/43706 (Novo Nordisk A/S), WO 99/43707 (Novo Nordisk A/S), WO 98/08871 (Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.), EP 0708179-A2 (Eli Lilly & Co.), EP 0699686-A2 (Eli Lilly & Co.), WO 01/98331 (Eli Lilly & Co).

In one embodiment, the GLP-1 agonist is a derivative of GLP-1(7-36)-amide, GLP-1(7-37), a GLP-1(7-36)-amide analogue or a GLP-1(7-37) analogue, which comprises a lipophilic substituent.

In this embodiment of the invention, the GLP-1 derivative preferably has three lipophilic substituents, more preferably two lipophilic substituents, and most preferably one lipophilic substituent attached to the parent peptide (ie GLP-1 (7-36)-amide, GLP-1(7-37), a GLP-1(7-36)-amide analogue or a GLP-1(7-37) analogue), where each lipophilic substituent(s) preferably has 4-40 carbon atoms, more preferably 8-30 carbon atoms, even more preferably 8-25 carbon atoms, even more preferably 12-25 carbon atoms, and most preferably 14-18 carbon atoms.

In one embodiment, the lipophilic substituent comprises a partially or completely hydrogenated cyclopentanophenathrene skeleton.

In another embodiment, the lipophilic substituent is a straight-chain or branched alkyl group.

In yet another embodiment, the lipophilic substituent is an acyl group of a straight-chain or branched fatty acid. Preferably, the lipophilic substituent is an acyl group having the formula $CH_3(CH_2)_nCO-$, wherein n is an integer from 4 to 38, preferably an integer from 12 to 38, and most preferably is $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$. In a more preferred embodiment, the lipophilic substituent is tetradecanoyl. In a most preferred embodiment, the lipophilic substituent is hexadecanoyl.

In a further embodiment of the present invention, the lipophilic substituent has a group which is negatively charged such as a carboxylic acid group. For example, the lipophilic substituent may be an acyl group of a straight-chain or branched alkane α,ω-dicarboxylic acid of the formula $HOOC(CH_2)_mCO-$, wherein m is an integer from 4 to 38, preferably an integer from 12 to 38, and most preferably is $HOOC(CH_2)_{14}CO-$, $HOOC(CH_2)_{16}CO-$, $HOOC(CH_2)_{18}CO-$, $HOOC(CH_2)_{20}CO-$ or $HOOC(CH_2)_{22}CO-$.

In the GLP-1 derivatives of the invention, the lipophilic substituent(s) contain a functional group which can be attached to one of the following functional groups of an amino acid of the parent GLP-1 peptide:

(a) the amino group attached to the alpha-carbon of the N-terminal amino acid, (b) the carboxy group attached to the alpha-carbon of the C-terminal amino acid, (c) the epsilon-amino group of any Lys residue, (d) the carboxy group of the R group of any Asp and Glu residue, (e) the hydroxy group of the R group of any Tyr, Ser and Thr residue, (f) the amino group of the R group of any Trp, Asn, Gln, Arg, and His residue, or (g) the thiol group of the R group of any Cys residue.

In one embodiment, a lipophilic substituent is attached to the carboxy group of the R group of any Asp and Glu residue.

In another embodiment, a lipophilic substituent is attached to the carboxy group attached to the alpha-carbon of the C-terminal amino acid.

In a most preferred embodiment, a lipophilic substituent is attached to the epsilon-amino group of any Lys residue.

In a preferred embodiment of the invention, the lipophilic substituent is attached to the parent GLP-1 peptide by means of a spacer. A spacer must contain at least two functional groups, one to attach to a functional group of the lipophilic substituent and the other to a functional group of the parent GLP-1 peptide.

In one embodiment, the spacer is an amino acid residue except Cys or Met, or a dipeptide such as Gly-Lys. For purposes of the present invention, the phrase "a dipeptide such as Gly-Lys" means any combination of two amino acids except Cys or Met, preferably a dipeptide wherein the C-terminal amino acid residue is Lys, His or Trp, preferably Lys, and the N-terminal amino acid residue is Ala, Arg, Asp, Asn, Gly, Glu, Gln, Ile, Leu, Val, Phe, Pro, Ser, Tyr, Thr, Lys, His and Trp. Preferably, an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

Preferred spacers are lysyl, glutamyl, asparagyl, glycyl, beta-alanyl and gamma-aminobutanoyl, each of which constitutes an individual embodiment. Most preferred spacers are glutamyl and beta-alanyl. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the E-amino group of Lys and the lipophilic substituent. In one embodiment, such a further spacer is succinic acid which forms an amide bond with the E-amino group of Lys and with an amino group present in the lipophilic substituent. In another embodiment such a further spacer is Glu or Asp which forms an amide bond with the E-amino group of Lys and another amide bond with a carboxyl group present in the lipophilic substituent, that is, the lipophilic substituent is a $N^\epsilon$-acylated lysine residue.

In another embodiment, the spacer is an unbranched alkane α,ω-dicarboxylic acid group having from 1 to 7 methylene groups, which spacer forms a bridge between an amino group of the parent peptide and an amino group of the lipophilic substituent. Preferably, the spacer is succinic acid.

In a further embodiment, the lipophilic substituent with the attached spacer is a group of the formula $CH_3(CH_2)_pNH-CO(CH_2)_qCO-$, wherein p is an integer from 8 to 33, preferably from 12 to 28 and q is an integer from 1 to 6, preferably 2.

In a further embodiment, the lipophilic substituent with the attached spacer is a group of the formula $CH_3(CH_2)_rCO-NHCH(COOH)(CH_2)_2CO-$, wherein r is an integer from 4 to 24, preferably from 10 to 24.

In a further embodiment, the lipophilic substituent with the attached spacer is a group of the formula $CH_3(CH_2)_sCO-NHCH((CH_2)_2COOH)CO-$, wherein s is an integer from 4 to 24, preferably from 10 to 24.

In a further embodiment, the lipophilic substituent is a group of the formula $COOH(CH_2)_tCO-$ wherein t is an integer from 6 to 24.

In a further embodiment, the lipophilic substituent with the attached spacer is a group of the formula $-NHCH(COOH)(CH_2)_4NH-CO(CH_2)_uCH_3$, wherein u is an integer from 8 to 18.

In a further embodiment, the lipophilic substituent with the attached spacer is a group of the formula $CH_3(CH_2)_vCO-NH-(CH_2)_z-CO$, wherein v is an integer from 4 to 24 and z is an integer from 1 to 6.

In a further embodiment, the lipophilic substituent with the attached spacer is a group of the formula $-NHCH(COOH)(CH_2)_4NH-COCH((CH_2)_2COOH)NH-CO(CH_2)_wCH_3$, wherein w is an integer from 10 to 16.

In a further embodiment, the lipophilic substituent with the attached spacer is a group of the formula $-NHCH(COOH)(CH_2)_4NH-CO(CH_2)_2CH(COOH)NHCO(CH_2)_xCH_3$, wherein x is zero or an integer from 1 to 22, preferably 10 to 16.

In yet another embodiment the GLP-1 agonist is $Arg^{34}$, $Lys^{26}(N^\epsilon-(\gamma-Glu(N^\alpha-hexadecanoyl)))$-GLP-1(7-37).

In yet another embodiment the GLP-1 agonist is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), analogues thereof and derivatives of any of these.

In yet another embodiment the GLP-1 agonist is selected from the group consisting of $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}$-GLP-1(7-37); $Arg^{26,34}Lys^{40}$-GLP-1(7-37); $Arg^{26}Lys^{36}$-GLP-1(7-37); $Arg^{34}Lys^{36}$-GLP-1(7-37); $Val^8Arg^{22}$-GLP-1(7-37); $Met^8Arg^{22}$-GLP-1(7-37); $Gly^8His^{22}$-GLP-1(7-37); $Val^8His^{22}$-GLP-1(7-37);

Met$^8$His$^{22}$-GLP-1(7-37); His$^{37}$-GLP-1(7-37); Gly$^8$-GLP-1(7-37); Val$^8$-GLP-1(7-37); Met$^8$-GLP-1(7-37); Gly$^8$Asp$^{22}$-GLP-1(7-37); Val$^8$Asp$^{22}$-GLP-1(7-37); Met$^8$Asp$^{22}$-GLP-1(7-37); Gly$^8$Glu$^{22}$-GLP-1(7-37); Val$^8$Glu$^{22}$-GLP-1(7-37); Met$^8$Glu$^{22}$-GLP-1(7-37); Gly$^8$Lys$^{22}$-GLP-1(7-37); Val$^8$Lys$^{22}$-GLP-1(7-37); Met$^8$Lys$^{22}$-GLP-1(7-37); Gly$^8$Arg$^{22}$-GLP-1(7-37); Val$^8$Lys$^{22}$His$^{37}$-GLP-1(7-37); Gly$^8$Glu$^{22}$His$^{37}$-GLP-1(7-37); Val$^8$Glu$^{22}$His$^{37}$-GLP-1(7-37); Met$^8$Glu$^{22}$His$^{37}$-GLP-1(7-37); Gly$^8$Lys$^{22}$ His$^{37}$-GLP-1(7-37); Met$^8$Lys$^{22}$His$^{37}$-GLP-1(7-37); Gly$^8$Arg$^{22}$His$^{37}$-GLP-1(7-37); Val$^8$Arg$^{22}$His$^{37}$-GLP-1(7-37); Met$^8$Arg$^{22}$His$^{37}$-GLP-1(7-37); Gly$^8$His$^{22}$His$^{37}$-GLP-1(7-37); Val$^8$His$^{22}$His$^{37}$-GLP-1(7-37); Met$^8$His$^{22}$His$^{37}$-GLP-1(7-37); Gly$^8$His$^{37}$-GLP-1(7-37); Val$^8$His$^{37}$-GLP-1(7-37); Met$^8$His$^{37}$-GLP-1(7-37); Gly$^8$Asp$^{22}$ His$^{37}$-GLP-1(7-37); Val$^8$Asp$^{22}$His$^{37}$-GLP-1(7-37); Met$^8$Asp$^{22}$His$^{37}$-GLP-1(7-37); Arg$^{26}$-GLP-1(7-36)-amide; Arg$^{34}$-GLP-1(7-36)-amide; Lys$^{36}$-GLP-1(7-36)-amide; Arg$^{26,34}$Lye-GLP-1(7-36)-amide; Arg$^{26,34}$-GLP-1(7-36)-amide; Arg$^{26,34}$Lys$^{40}$-GLP-1(7-36)-amide; Arg$^{26}$Lye-GLP-1(7-36)-amide; Arg$^{34}$Lys$^{36}$-GLP-1(7-36)-amide; Gly$^8$-GLP-1(7-36)-amide; Val$^8$-GLP-1(7-36)-amide; Met$^8$-GLP-1(7-36)-amide; Gly$^8$Asp$^{22}$-GLP-1(7-36)-amide; Gly$^8$Glu$^{22}$His$^{37}$-GLP-1(7-36)-amide; Val$^8$Asp$^{22}$-GLP-1(7-36)-amide; Met$^8$Asp$^{22}$-GLP-1(7-36)-amide; Gly$^8$Glu$^{22}$-GLP-1(7-36)-amide; Val$^8$Glu$^{22}$-GLP-1(7-36)-amide; Met$^8$Glu$^{22}$-GLP-1(7-36)-amide; Gly$^8$Lys$^{22}$-GLP-1(7-36)-amide; Val$^8$Lys$^{22}$-GLP-1(7-36)-amide; Met$^8$Lys$^{22}$-GLP-1(7-36)-amide; Gly$^8$His$^{22}$His$^{37}$-GLP-1(7-36)-amide; Gly$^8$Arg$^{22}$-GLP-1(7-36)-amide; Val$^8$Arg$^{22}$-GLP-1(7-36)-amide; Met$^8$Arg$^{22}$-GLP-1(7-36)-amide; Gly$^8$His$^{22}$-GLP-1(7-36)-amide; Val$^8$His$^{22}$-GLP-1(7-36)-amide; Met$^8$His$^{22}$-GLP-1(7-36)-amide; His$^{37}$-GLP-1(7-36)-amide; Val$^8$Arg$^{22}$His$^{37}$-GLP-1(7-36)-amide; Met$^8$Arg$^{22}$His$^{37}$-GLP-1(7-36)-amide; Gly$^8$His$^{37}$-GLP-1(7-36)-amide; Val$^8$His$^{37}$-GLP-1(7-36)-amide; Met$^8$His$^{37}$-GLP-1(7-36)-amide; Gly$^8$Asp$^{22}$ His$^{37}$-GLP-1(7-36)-amide; Val$^8$Asp$^{22}$His$^{37}$-GLP-1(7-36)-amide; Met$^8$Asp$^{22}$His$^{37}$-GLP-1(7-36)-amide; Val$^8$Glu$^{22}$His$^{37}$-GLP-1(7-36)-amide; Met$^8$Glu$^{22}$His$^{37}$-GLP-1(7-36)-amide; Gly$^8$Lys$^{22}$ His$^{37}$-GLP-1(7-36)-amide; Val$^8$Lys$^{22}$His$^{37}$-GLP-1(7-36)-amide; Met$^8$Lys$^{22}$His$^{37}$-GLP-1(7-36)-amide; Gly$^8$Arg$^{22}$His$^{37}$-GLP-1(7-36)-amide; Val$^8$His$^{22}$His$^{37}$-GLP-1(7-36)-amide; Met$^8$His$^{22}$His$^{37}$-GLP-1(7-36)-amide; and derivatives thereof.

In yet another embodiment the GLP-1 agonist is selected from the group consisting of Val$^8$Trp$^{19}$Glu$^{22}$-GLP-1(7-37), Val$^8$Glu$^{22}$Val$^{25}$-GLP-1(7-37), Val$^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$His$^{37}$-GLP-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37), analogues thereof and derivatives of any of these.

In yet another embodiment the GLP-1 agonist is a stable GLP-1 analogue/derivative. Throughout this application a "stable GLP-1 analogue/derivative" means a GLP-1 analogue or a derivative of a GLP-1 analogue which exhibits an in vivo plasma elimination half-life of at least 10 hours in man, as determined by the method described below. Examples of stable GLP-1 analogue/derivatives can be found in WO 98/08871 and WO 99/43706. The method for determination of plasma elimination half-life of a compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

Stable GLP-1 analogues and derivatives are disclosed in WO 98/08871 (analogues with lipophilic substituent) and in WO 02/46227 (analogues fused to serum albumin or to Fc portion of an Ig).

In another embodiment, The GLP-1 agonist is formulated so as to have a half-life in man, as discussed above, of at least 10 hours. This may be obtained by sustained release formulations known in the art.

In yet another embodiment the GLP-1 agonist is exendin-4 or exendin-3, an exendin-4 or exendin-3 analogue or a derivative of any of these.

Examples of exendins as well as analogues, derivatives, and fragments thereof to be included within the present invention are those disclosed in WO 97/46584, U.S. Pat. No. 5,424,286 and WO 01/04156. U.S. Pat. No. 5,424,286 describes a method for stimulating insulin release with an exendin polypeptide. The exendin polypeptides disclosed include HGEGTFTSDLSKQMEEEAVRL-FIEWLKNGGX; wherein X=P or Y, and HX1X2GTFITS-DLSKQMEEEAVRLFIEWLKNGGPSSGAPPPS; wherein X1X2=SD (exendin-3) or GE (exendin-4)). WO 97/46584 describes truncated versions of exendin peptide(s). The disclosed peptides increase secretion and biosynthesis of insulin, but reduce those of glucagon. WO 01/04156 describes exendin-4 analogues and derivatives as well as the preparation of these molecules. Exendin-4 analogues stabilized by fusion to serum albumin or Fc portion of an Ig are disclosed in WO 02/46227.

In one embodiment, the exendin-4 analogue is HGEGT-FTSDLSKQMEEEAVRL-FIEWLKNGGPSSGAPPSKKK-KKK.

In yet another embodiment the GLP-1 agonist is a stable exendin-4 analogue/-derivative. The term "stable exendin-4 analogue/derivative", as used herein refers to an exendin-4 (1-39) analogue or a derivative of an exendin-4(1-39) analogue which exhibits an in vivo plasma elimination half-life of at least 10 hours in man, as determined by the method described above for a "stable GLP-1 analogue/derivative".

In still another embodiment, the GLP-1 agonist is Aib$^{8,35}$ GLP-1(7-36) amide (Aib=α-amino isobutyric acid).

In still another embodiment, the GLP-1 agonist is Ser$^{38}$, Lys$^{39,40,41,42,43,44}$-Exendin-4(1-39)amide.

In still another embodiment the GLP-1 agonist is selected from the non-peptide small molecule GLP-1 agonists disclosed in WO 00/42026.

The present invention also encompasses pharmaceutically acceptable salts of the GLP-1 agonists. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present GLP-1 agonists are able to form.

Peptide GLP-1 compounds can be produced by appropriate derivatization of an appropriate peptide backbone which has been produced by recombinant DNA technology or by peptide synthesis (e.g. Merrifield-type solid phase synthesis) as known in the art of peptide synthesis and peptide chemistry.

The route of administration of GLP-1 agonists may be any route which effectively transports the active compound to the appropriate or desired site of action, such as oral, nasal, buccal, pulmonal, transdermal or parenteral.

Medicaments or pharmaceutical compositions containing a GLP-1 agonist such as $Arg^{34}$, $Lys^{26}(N^{\epsilon}-(\gamma-Glu(N^{\alpha}-hexadecanoyl)))$-GLP-1(7-37) may be administered parenterally to a patient in need thereof. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of a GLP-1 agonist in the form of a nasal or pulmonal spray. As a still further option, the GLP-1 agonist can also be administered transdermally, e.g. from a patch, optionally an iontophoretic patch, or transmucosally, e.g. bucally. The above-mentioned possible ways to administer GLP-1 agonists are not considered as limiting the scope of the invention.

In one embodiment, the dosage of GLP-1 agonist to be administered to a patient in a method of the invention is from about 0.1 ug/kg/day to about 20 ug/kg/day.

In another embodiment, the dosage of GLP-1 agonist to be administered to a patient in a method of the invention is from about 0.5 ug/kg/day to about 2 ug/kg/day.

In one embodiment, A GLP-1 agonist is co-administered together with further therapeutically active compound used in the treatment of obesity or to induce weight loss or to maintain an obtained weight loss, or used in the treatment of diseases or states where obesity is part of the etiology. Examples of further therapeutically active compounds include antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells e.g. potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, glucokinase activators, such as those described in WO 02/08209 to Hoffmann La Roche, inhibitors of hepatic enzymes involved in stimulation of gluconeogenesis and/or glycogenolysis, glucose intake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

Other examples of suitable additional therapeutically active compounds include insulin or insulin analogues, sulfonylurea e.g. tolbutamide, chlorpropamide, tolazamide, glibenclamide, glipizide, glimepiride, glicazide, glyburide, biguanide e.g. metformin, meglitinide e.g. repaglinide or senaglinide/nateglinide.

Other examples of suitable additional therapeutically active compounds include thiazolidinedione insulin sensitizer e.g. troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

Other examples of suitable additional therapeutically active compounds include insulin sensitizer e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

Other examples of suitable additional therapeutically active compounds include α-glucosidase inhibitor e.g. voglibose, emiglitate, miglitol or acarbose.

Other examples of suitable additional therapeutically active compounds include glycogen phosphorylase inhibitor e.g. the compounds described in WO 97/09040 (Novo Nordisk A/S).

Other examples of suitable additional therapeutically active compounds include a glucokinase activator.

Other examples of suitable additional therapeutically active compounds include an agent acting on the ATP-dependent potassium channel of the pancreatic β-cells e.g. tolbutamide, glibenclamide, glipizide, glicazide, BTS-67582 or repaglinide.

Other examples of suitable additional therapeutically active compounds include nateglinide.

Other examples of suitable additional therapeutically active compounds include an antihyperlipidemic agent or a antilipidemic agent e.g. cholestyramine, colestipol, clofibrate, gemfibrozil, lovastatin, pravastatin, simvastatin, probucol or dextrothyroxine.

Other examples of said additional therapeutically active compounds include antiobesity compounds or appetite regulating agents. Such compounds may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, chemical uncouplers, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists and ciliary neurotrophic factor. Further antiobesity agents are bupropion (antidepressant), topiramate (anticonvulsant), ecopipam (dopamine D1/D5 antagonist), naltrexone (opioid antagonist), and peptide $YY_{3-36}$ (Batterham et al, Nature 418, 650-654 (2002)).

In one embodiment, the antiobesity agent is leptin.

In one embodiment, the antiobesity agent is peptide $YY_{3-36}$.

In one embodiment, the antiobesity agent is a serotonin and norepinephrine reuptake inhibitor e.g. sibutramine.

In one embodiment, the antiobesity agent is a lipase inhibitor e.g. orlistat.

In one embodiment, the antiobesity agent is an adrenergic CNS stimulating agent e.g. dexamphetamine, amphetamine, phentermine, mazindol phendimetrazine, diethylpropion, fenfluramine or dexfenfluramine.

In one embodiment, the antiobesity agent is oxynthomodulin, as disclosed in WO 03/22304 (Imperial College).

In one embodiment, the antiobesity agent is a ghrelin antagoninst, e.g. as disclosed in WO 01/56592.

In one embodiment, the antiobesity agent is an energy expenditure modifier.

In one embodiment, the antiobesity agent is a 11β-Hydroxysteroid Dehydrogenase Type 1 Inhibitor.

Other examples of suitable additional therapeutically active compounds include anti-hypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and a-blockers such as doxazosin, urapidil, prazosin and terazosin.

Pharmaceutical Compositions

Pharmaceutical compositions containing GLP-1 agonists such as $Arg^{34}$, $Lys^{26}(N^{\epsilon}-(\gamma-Glu(N^{\alpha}-hexadecanoyl)))$-GLP-1 (7-37) may be prepared by conventional techniques, e.g. as described in *Remington's Pharmaceutical Sciences*, 1985 or in *Remington: The Science and Practice of Pharmacy*, $19^{th}$ edition, 1995.

Thus, injectable compositions of GLP-1 agonists, insulin and autoimmune agents can be prepared using the conventional techniques of the pharmaceutical industry which involves dissolving and mixing the ingredients as appropriate to give the desired end product.

For example, a GLP-1 agonist such as $Arg^{34}$, $Lys^{26}(N^{\epsilon}-(\gamma-Glu(N^{\alpha}-hexadecanoyl)))$-GLP-1(7-37) may be dissolved in an amount of water which is somewhat less than the final volume of the composition to be prepared. An isotonicity agent, a preservative and a buffer are added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In one embodiment of the invention, the formulation of the GLP-1 agonist has a pH in the range from 7.0 to 10. In another embodiment of the invention the formulation has a pH in the range from 7.0 to 9.5. In a further embodiment of the invention the formulation has a pH in the range from 7.0 to 8.5. In yet another embodiment of the invention the formulation has a pH in the range from 7.0 to 8.0, preferably from 7.4 to 7.8. In a further embodiment of the invention the formulation has a pH in the range from 9.0 to 10.

Examples of isotonic agents to be used in the formulations of the invention are those selected from the group consisting of a salt (e.g. sodium chloride), a polyhydric alcohol (e.g., xylitol, mannitol, sorbitol or glycerol), a monosaccharide (e.g. glucose or maltose), a disaccharide (e.g. sucrose), an amino acid (e.g. L-glycine, L-histidine, arginine, lysine, isoleucine, aspartic acid, tryptophan, threonine), polyethyleneglycol (e.g. PEG400), propylene glycol, or mixtures thereof. In a further embodiment of the invention the isotonic agent is selected from the group consisting of sodium chloride, glycerol, mannitol, glucose, sucrose, L-glycine, L-histidine, arginine, lysine or mixtures thereof. Each one of these specific isotonic agents constitutes an alternative embodiment of the invention.

Examples of preservatives to be used in the formulations of the invention are phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol.

Examples of suitable buffers to be used in the formulations of the invention are sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a preferred embodiment of the invention the buffer is glycylglycine, sodium dihydrogen phosphate, disodium hydrogen phosphate, sodium phosphate or mixtures thereof.

Further to the above-mentioned components, solutions containing a GLP-1 agonist may also contain a surfactant in order to improve the solubility and/or the stability of the peptide. In a further embodiment of the invention the formulation further comprises a surfactant. In a further embodiment of the invention the surfactant is selected from a detergent, ethoxylated castor oil, polyglycolized glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium taurodihydrofusidate etc.), long-chain fatty acids and salts thereof C6-C12 (eg. oleic acid and caprylic acid), acylcarnitines and derivatives, $N^{\alpha}$-acylated derivatives of lysine, arginine or histidine, or side-chain acylated derivatives of lysine or arginine, $N^{\alpha}$-acylated derivatives of dipeptides comprising any combination of lysine, arginine or histidine and a neutral or acidic amino acid, $N^{\alpha}$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of isotonicity agents, preservatives, and surfactants are well known in the pharmaceutical arts and reference is made to Remington: *The Science and Practice of Pharmacy*, $20^{th}$ edition, 2000.

In a further embodiment of the invention the GLP-1 agonist is present in a formulation of the invention in a concentration from 0.1 mg/ml to 80 mg/ml. In a further embodiment of the invention the GLP-1 agonist is present in a concentration from 1 mg/ml to 80 mg/ml. In a further embodiment of the invention the GLP-1 agonist is present in a concentration from 0.1 mg/ml to 50 mg/ml. In a further embodiment of the invention the GLP-1 agonist is present in a concentration from 1 mg/ml to 50 mg/ml. In a further embodiment of the invention the GLP-1 agonist is present in a concentration from 0.1 mg/ml to 20 mg/ml. In a further embodiment of the invention the GLP-1 agonist is present in a concentration from 1 mg/ml to 20 mg/ml. In a further embodiment of the invention the GLP-1 agonist is present in a concentration from 0.1 mg/ml to 10 mg/ml. In a further embodiment of the invention the GLP-1 agonist is present in a concentration from 1 mg/ml to 10 mg/ml. In a further embodiment of the invention the GLP-1 agonist is present in a concentration from 0.1-5 mg/ml. In a further embodiment of the invention the GLP-1 agonist is present in a concentration from 1-5 mg/ml. In a further embodiment of the invention the GLP-1 agonist is present in a concentration from 0.1-0.5 mg/ml. In a further embodiment of the invention the GLP-1 agonist is present in a concentration from 0.6-1 mg/ml. Each one of these specific concentration ranges constitutes an alternative embodiment of the invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Diet induced obesity (DIO) was introduced over 2½ months, by feeding 4 months old rats a diet consisting of chow and 5 alternating kinds of candy (chocolate, chocolate biscuits, sugar). The candy was changed every day, so that the same candy was offered every fifth day. A lean control group was fed chow only. In the DIO group this was followed by a 12-week treatment with liraglutide (0.2 mg/kg s.c. bid, n=10). The candy and chow offer was continued for the whole treatment period also. Vehicle was given to both obese (n=14) and lean control rats (n=15). Food intake, differentiated between chow and candy, was monitored daily.

Liraglutide significantly (p=0.009) reduced total cumulated caloric intake (4452.3±150.6 vs. 5061.2±99.9 kcal). This reduction was a selective reduction in calories obtained from candy (2863.3±200.9 vs. 3803.2±110.2 kcal, p=0.017), since there was actually an increase in calories obtained from chow (1589.0±96.9 vs. 1248.5±71.6 kcal, p=0.001).

Liraglutide is the IND name for $Arg^{34}$, $Lys^{26}(N^{\epsilon}\text{-}(\gamma\text{-Glu}(N^{\epsilon}\text{-hexadecanoyl})))$-GLP-1(7-37); Candy 1 (sugar): mono- and di-saccharides constituted 100% of the total amount of carbohydrate; candy 2 (chocolate cream filled crackers): Glycemic index 49%, 39% of the total energy stems from fat, mono- and di-saccharides constitute 57% of the total amount of carbohydrates; candy 3 (milk chocolate): Glycemic index 49%, 60% of the total energy stems from fat, mono- and di-saccharides constitute 90% of the total amount of carbohydrates; candy 4 (milk chocolate with nuts): 80% of the total energy stems from fat, mono- and di-saccharides constitute 80% of the total amount of carbohydrates; candy 5 (toffee chocolate): 80% of the total energy stems from fat, mono- and di-saccharides constitute 75% of the total amount of carbohydrates; chow: 15% of the total energy stems from fat, mono- and di-saccharides constitute 15% of the total amount of carbohydrates;

The data clearly shows that GLP-1 agonists are capable of reducing the intake of calories, and also that GLP-1 agonists induce a dislike for food with a high glycemic index or wherein the mono- and di-saccharides together constitute a large proportion of the total carbohydrate amount.

Example 2

An experiment showing the effect of GLP-1 agonists in humans may be designed as described here. Human subjects are administered one or several daily dose(s) of a GLP-1 agonist leading to pharmacological active GLP-1-like levels in the blood or a placebo compound. The subjects are given a choice of foods and drink from one or more of the groups A) to D) and one or more from the groups E) to H).

A) The glycemic index is above 60%
B) The glycemic index is above 40% and wherein more than 30% of the total amount of energy stems from fat
C) The amount of mono- or di-saccharides together constitute more than 25% of total carbohydrate content
D) The amount of mono- or di-saccharides together constitute more than 25% of total carbohydrate content and wherein more than 30% of the total amount of energy stems from fat
E) The glycemic index is below 60%
F) The glycemic index is below 40% and wherein less than 30% of the total amount of energy stems from fat
G) The amount of mono- and di-saccharides together constitute together constitute less than 25% of the total carbohydrate content
H) The amount of mono- and di-saccharides together constitute together constitute less than 25% of the total carbohydrate content, and wherein less than 30% of the total amount of energy stems from fat The amount eaten and drunk of all groups of food is calculated in terms of energy intake, and the ability of the GLP-1 agonist to selectively decrease intake of the food from one or more of the groups A) to D) (unhealthy food) and increase the intake of food from one or more of the groups E) to H) (healthy food) is calculated.

The invention claimed is:

1. A method for shifting food preference in a subject with an abnormal or excessive intake of food, comprising administering to the subject an effective amount of $Arg^{34}$, $Lys^{26}(N^{\epsilon}$-($\gamma$-Glu($N^{\epsilon}$-hexadecanoyl)))-GLP-1(7-37); wherein the subject is obese and has a BMI greater than 25;
wherein the abnormal or excessive intake of food is of a first food comprising a glycemic index above 40%, wherein more than 30% of the total energy in said first food stems from fat, and a second food comprising mono- and di-saccharides that together constitute more than 50% of the total amount of carbohydrate in said second food; and
wherein the food preference is shifted away from the first food and the second food.

2. The method according to claim 1, wherein the $Arg^{34}$, $Lys^{26}(N^{\epsilon}$-($\gamma$-Glu($N^{\epsilon}$-hexadecanoyl)))-GLP-1(7-37) is administered in connection with a meal.

* * * * *

SEQUENCE LISTING

```
<160> NUMBER OF SEQ ID NOS: 3

<210> SEQ ID NO 1
<211> LENGTH: 31
<212> TYPE: PRT
<213> ORGANISM: Gila Monster
<220> FEATURE:
<221> NAME/KEY: MISC_FEATURE
<222> LOCATION: (31)..(31)
<223> OTHER INFORMATION: X= P or Y

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 2
<211> LENGTH: 40
<212> TYPE: PRT
<213> ORGANISM: Gila Monster
<220> FEATURE:
<221> NAME/KEY: MISC_FEATURE
<222> LOCATION: (2)..(2)
<223> OTHER INFORMATION: X=S or G
<220> FEATURE:
<221> NAME/KEY: MISC_FEATURE
<222> LOCATION: (3)..(3)
<223> OTHER INFORMATION: X=D or E

<400> SEQUENCE: 2

His Xaa Xaa Gly Thr Phe Ile Thr Ser Asp Leu Ser Lys Gln Met Glu
1               5                   10                  15
```

```
Glu Glu Ala Val Arg Leu Phe Ile Glu Trp Leu Lys Asn Gly Gly Pro
            20                  25                  30

Ser Ser Gly Ala Pro Pro Pro Ser
            35                  40

<210> SEQ ID NO 3
<211> LENGTH: 44
<212> TYPE: PRT
<213> ORGANISM: Artificial
<220> FEATURE:
<223> OTHER INFORMATION: Synthetic

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
            35                  40
```